ized Patent [19] 3,935,068
Nystrom                                    [45] Jan. 27, 1976

| [54] | CONTINUOUS ISOMERIZATION PROCESS UTILIZING IMMOBILIZED FLOCCULATE ENZYME |
|---|---|
| [75] | Inventor: Charles W. Nystrom, Winston-Salem, N.C. |
| [73] | Assignee: R. J. Reynolds Tobacco Company, Winston-Salem, N.C. |
| [22] | Filed: Jan. 2, 1973 |
| [21] | Appl. No.: 320,035 |
| [52] | U.S. Cl. .................. 195/31 F; 195/63; 195/68; 195/115; 195/DIG. 11 |
| [51] | Int. Cl.² .................................. C12D 13/00 |
| [58] | Field of Search .......... 195/31 F, 68, 63, 115, 195/DIG. 11 |

[56]            References Cited
          UNITED STATES PATENTS

| 3,594,325 | 7/1971 | Feierstein et al. ............... 195/63 |
| 3,645,848 | 2/1972 | Lee et al. ........................ 195/31 |
| 3,695,999 | 10/1972 | Forgione et al. ................ 195/63 |
| 3,788,945 | 1/1974 | Thompson et al. .............. 195/63 |
| 3,791,927 | 2/1974 | Forgione et al. ................ 195/68 |

Primary Examiner—Alvin E. Tanenholtz
Assistant Examiner—Thomas G. Wiseman
Attorney, Agent, or Firm—Manford R. Haxton; Hebert J. Bluhm

[57]             ABSTRACT

Cell-free active enzyme preparations are treated with flocculating agents to produce aggregates that are useful in effecting enzyme-catalyzed chemical transformations. Substrates are brought into contact with the aggregates where they undergo chemical transformations in the presence of the active enzymes.

5 Claims, No Drawings

CONTINUOUS ISOMERIZATION PROCESS UTILIZING IMMOBILIZED FLOCCULATE ENZYME

SUMMARY OF THE INVENTION

This invention relates to a process for effecting chemical transformation of various substrates in the presence of enzymes which have been previously immobilized by treatment with flocculating agents. More specifically, cell-free enzyme preparations are treated with polyelectrolyte flocculating agents under conditions favoring formation of stable enzyme-containing aggregates. Inert support materials are preferably incorporated into the aggregates to produce a material that is particularly suitable for use in continuous enzymatic processes in which a substrate solution is passed through a bed of the aggregates.

BACKGROUND OF THE INVENTION

The use of enzymes to effect specific chemical transformations is well known. In carrying out such transformations, cell-free preparations are commonly employed in batch-type processes. The rather costly procedures normally used in the production of cell-free enzyme preparations raises questions of economic feasibility in view of the fact that the enzymes are used one time only in batch-type operations. It is this fact which has prompted an increased interest in the preparation of various forms of immobilized enzymes which would permit repeated use of the enzymes thus making such processes commercially attractive.

A number of immobilizing agents for enzymes have been investigated but a totally satisfactory process which is generally applicable to a large number of enzymes has not yet been found. Various problems such as enzyme inactivation resulting from the immobilization procedure, low substrate flow rates through the immobilized enzyme and difficulty in purifying enzymes prior to immobilization have prevented wide commercial use of continuous-type processes based on immobilized enzymes. The present invention provides a simple, convenient and effective means of adapting enzymes for use in either continuous or batch-type operations which largely overcomes the foregoing limitations. It has been found that cell-free enzyme preparations can be easily converted to stable enzyme-containing aggregates through the use of polyelectrolyte flocculating materials. The process disclosed herein does not require enzyme purification, enzyme inactivation is minimal and the immobilized enzyme material prepared in the presence of an inert support material is characterized by a loose, noncompacting mass which allows relatively high flow rates of substrate solution through the enzyme reactor bed. Moreover, this immobilization procedure can be adapted to a wide variety of enzymes and enzymatic processes, enzymes from plant or animal sources being equally amenable to the disclosed procedure.

DETAILED DESCRIPTION OF THE INVENTION

Briefly, this invention involves the use of polyelectrolytes as aggregate-forming flocculants for cell-free enzyme preparations. The enzyme-containing aggregates are preferably formed in the presence of inert filter aids and the material thus obtained is packed into a column or formed into some other suitable reactor bed through which a substrate solution is passed to effect the desired chemical transformation.

The polyelectrolytes contemplated for use with this process are preferably water-soluble polymeric substances containing monomeric units which possess polar or ionizable groups. They are generally classified into three main categories — anionic, cationic and nonionic. Anionic polyelectrolytes usually contain carboxylic, sulfonic or phosphonic acid groups and examples of such materials include polyacrylic acid, polystyrenesulfonic acid, polyvinylphosphonic acid, alginic acid and pectic acid. Most cationic polyelectrolytes involve the use of quaternary ammonium, sulfonium or phosphonium groups including the protonated forms of polyamines such as polyethylenimine and polyvinylpyridine. Specific examples of synthetic cationic polyelectrolytes may be found in a comprehensive review by M. F. Hoover, J. Macromol. Sci.—Chem. A4(6), pp. 1327–1417 (1970). Nonionic polyelectrolytes are exemplified by polyacrylamide and polyvinyl alcohol. Obviously, polyelectrolytes having characteristics of more than one of the above categories may also be used in the process disclosed herein. For example, partial hydrolysis of polyacrylamide would produce a polyelectrolyte having both amide (nonionic) and carboxylic acid (anionic) groups.

With respect to the foregoing categories of polyelectrolytes, it has been found that totally nonionic polyelectrolytes used alone are essentially ineffective as flocculants for cell-free enzyme preparations. However, nonionic or partially nonionic polyelectrolytes may be used in combination with anionic or cationic polyelectrolytes to give useful enzyme-containing aggregates. Accordingly, the polyelectrolytes which may be satisfactorily used for the process of this invention are water-soluble anionic or cationic polyelectrolytes, preferably of synthetic origin, as well as combinations of anionic, cationic and nonionic polyelectrolytes.

The formation of the flocculated cell-free enzyme is effected by adding a solution of the polyelectrolyte flocculant to a stirred, aqueous solution or suspension of the enzyme. Flocculation of the enzyme occurs almost immediately and the resulting aggregates are recovered by filtration or other suitable means.

In a particularly preferred embodiment of the invention, an inert filter aid is added to the enzyme-containing medium prior to addition of the flocculant. This results in a uniform distribution of the filter aid throughout the enzyme-containing aggregates and improves substrate solution flow rates through a bed of the aggregates when the latter is used in a continuous enzymatic process. By "inert filter aid" is meant a material which improves the filtration properties of the flocculated enzyme and which has no appreciable detrimental effect on either the activity of the enzyme or the stability of the substrate and product involved in the enzymatic process of interest. Typical of the filter aids which may be used are infusorial earth such as Celite (available from Johns-Manville of Baltimore, Maryland) and asbestos fibers. Also useful are water-insoluble polymeric adsorbents such as acrylic ester resins XAD-1 and XAD-4 available from Rohm and Haas of Philadelphia, Pennsylvania.

In another preferred embodiment of this invention, a cationic and an anionic polyelectrolyte are used sequentially to effect immobilization of the cell-free enzyme preparation. In most cases a superior floc is obtained if the cationic polyelectrolyte is added to the enzyme-containing medium before addition of the anionic polyelectrolyte. A filter aid may be used in conjunction with this embodiment also but it is not necessary.

The quantity of polyelectrolyte required will depend on the type or types used and the nature and amount of the enzyme being treated. In general, cationic or combinations of cationic and anionic flocculants are utilized in amounts sufficient to effect flocculation only. The flocculants are usually added in the form of dilute solutions or suspensions and the flocculation is preferably conducted at temperatures between about 10° and 40° C. The pH of the flocculation medium is determined by the stability of the enzyme and the optimum pH range in which the flocculant is effective. Optimum conditions for effecting flocculation are readily determined by experimentation.

The immobilized enzyme material obtained from the flocculation step may be dried for storage and later use or it may be used directly in preparing a reactor bed of suitable dimensions for use in a continuous enzymatic process. For example, a vertical column having a circular cross section and provided with means for heating the column may serve as a support for the reactor bed. The immobilized enzyme material is introduced into the column as an aqueous slurry or suspension and allowed to settle. Passage of a substrate solution or emulsion through the packed colulmn is then effected at a controlled flow rate to produce the desired chemical transformation of the substrate.

The immobilized enzyme material may be used for a wide variety of enzyme-catalyzed transformations such as isomerization, oxidation, dehydrogenation, hydrolysis and reduction. The quantity of enzyme-containing material required for a given process will depend on a number of factors including the specific enzyme activity of the material and its availability to the substrate as well as the rate and degree of transformation desired. Operating parameters such as temperature, pH and substrate concentration are readily determined by experimentation. The product of the enzyme-catalyzed transformation is recovered by any suitable means or subjected to further treatment as desired.

The following examples will further illustrate the process of this invention:

EXAMPLE 1

Fermentation of *Arthrobacter* nov. sp. NRRL B-3728 is carried out as described in U.S. Pat. No. 3,645,848 and the cells are harvested by centrifugation. A 10 percent by weight suspension of the harvested cells in 0.01 M Tris buffer (pH 8.2) and 0.001 M magnesium chloride is treated with crystalline lysozyme (0.05 mg. per gram of wet cells). The cell suspension is incubated at 60° C. for 2 hours with gentle agitation. The suspension is then cooled to 12° C. and subjected to sonication for 5 minutes. Centrifugation yields a clear, cell-free supernatant containing isomerase. A 200-milliliter portion of this supernatant containing 2 grams of Silflo filter aid (supplied by Silflo Corporation of Ft. Worth, Tex.) is slowly agitated at about 25° C. while adding to it 40 milliliters of a 1.5% solution of Primafloc C-7 cationic flocculant (supplied by Rohm & Haas) which has been previously adjusted to pH 8.0 by the addition of sodium hydroxide. Agitation is continued for a few minutes before collecting the enzyme-containing flocculated material by vacuum filtration. A 1.3-gram portion of this material is packed into a 1-inch diameter glass column and through it is passed a 50 weight percent solution of dextrose containing 0.004 M magnesium chloride and adjusted to pH 8.0. The column is maintained at 60° C. and the flow rate of the effluent syrup is controlled to give 440 milliliters per day. After one day the effluent syrup contains 16.1% fructose and after nine days contains 14.2% fructose thus demonstrating the stability of the flocculated enzyme.

EXAMPLE 2

Fermentation of *Streptomyces olivochromogenes* is carried out as described in U.S. Pat. No. 3,622,463 and the mycelia are harvested by centrifugation. One liter of a 10% by weight suspension of the harvested mycelia is homogenized in a Waring blendor for 2 minutes and is then subjected to sonication for 6 minutes. Centrifugation yields a clear, cell-free supernatant containing isomerase. To a stirred 200-milliliter portion of this supernatant are added 4 grams of Silflo filter aid and 20 milliliters of a 5% solution of Magnifloc 521C (a cationic flocculant supplied by American Cyanamid Company, Water-Treating Chemicals Department, Wayne, N.J. 07470). Immediately following addition of Magnifloc 521C, 30 milliliters of a 1% solution of Primafloc A-10 anionic flocculant (available from Rohm and Haas) are added. Stirring is continued for a few minutes and the flocculated enzyme is recovered by centrifugation to give 8 grams of wet material which, upon drying overnight at 56° C., yields 4.3 grams of dry material. A slurry of 3.3 grams of the dried, flocculated enzyme in 0.01 M sodium bicarbonate is packed in a 1-inch diameter glass column and heated to 60° C. A 50 weight percent solution of dextrose having pH 8.0 is passed through the column on a continuous basis at a flow rate of 450 milliliters per day. After one day the syrup emerging from the column contains 32.5% fructose and after 16 days it contains 24.0% fructose.

EXAMPLE 3

A cell-free extract containing glucose isomerase is prepared from *Arthrobacter* cells as described in Example 1. A 100-milliliter portion of the enzyme solution containing 10 grams of Celite is treated with 85 milliliters of a 5 percent solution of Magnifloc 521C. Gentle stirring of the flocculating medium is continued for a few minutes and the flocculated enzyme is then recovered by vacuum filtration. The enzyme-containing floc is packed into a column and a 94 DE starch conversion syrup containing 0.004 M magnesium chloride and buffered with Tris (pH 8.2) is passed through the column. The column is maintained at 60° C. and the flow rate is controlled to give 1175 milliliters per day. The initial glucose to frustose conversion is 46% and after 4 weeks of continuous operation the conversion rate is 34%.

EXAMPLE 4

A cell-free glucose isomerase preparation is obtained from *Arthrobacter* cells as described in Example 1. Flocculation of 750 milliliters of the isomerase solution in the presence of 50 grams of Celite using 300 millililters of 5% Purifloc C-31 (a polyethylenimine flocculant available from the Dow Chemical Company of Midland, Michigan) is effected as described in Example 3. The resulting flocculated isomerase is suitable for use in a continuous glucose isomerization process.

EXAMPLE 5

An experimental fungal lactose preparation (Lot No. 957-43 having 145 MLU/gm activity) obtained from Miles Laboratories, Inc. of Elkhart, Indiana is used to prepare 500 milliliters of a 0.2% by weight aqueous solution of the enzyme. To this solution are added, with gentle agitation, 10 grams of Silflo filter aid, 1.2 milliliters of a 1.5% solution of Primafloc C-7 (previously adjusted to pH 6.5) and 0.5 milliliter of a 1.5% solution of Primafloc A-10 in that order. The flocculated enzyme is recovered by filtration and dried to give 9.7 grams of immobilized enzyme. This material is formed into a suitable reactor bed through which is passed a 5% lactose solution containing 0.02 M acetate buffer (pH 4.5). The lactose in the feed solution is partially hydrolyzed to given an effluent containing glucose and galactose.

The advantages of this invention are readily apparent from the foregoing description. It will be appreciated that any number of variations in the basic process described herein may be made. The modifications and equivalents which fall within the spirit of the invention and scope of the appended claims are to be considered part of the invention.

What is claimed is:

1. A continuous process for converting glucose to fructose which comprises passing a glucose-containing solution through a bed of immobilized glucose isomerase wherein the immobilized glucose isomerase is used in the form of an aggregate comprising cell-free glucose isomerase and a water-soluble polyelectrolyte flocculating agent selected from the group consisting of cationic polyelectrolytes and anionic polyelectrolytes.

2. A process according to claim 1 in which said aggregate contains a filter aid.

3. A process according to claim 1 in which said glucose isomerase is derived from a microorganism belonging to the genus *Arthrobacter*.

4. A process according to claim 1 in which said glucose isomerase is derived from a microorganism belonging to the genus *Streptomyces*.

5. A process according to claim 1 in which said bed is maintained at a temperature between 50° and 90° C. and said glucose-containing solution has a pH of about 6 to 10.

* * * * *